(12) United States Patent
Cozzolino

(10) Patent No.: US 7,923,042 B2
(45) Date of Patent: Apr. 12, 2011

(54) MEDICATED GAUZE

(75) Inventor: Guglielmo Cozzolino, Montesarchio (IT)

(73) Assignee: Svas Biosana S.R.L., S. Giuseppe Vesuviano (IT)

( * ) Notice: Subject to any disclaimer, the term of this patent is extended or adjusted under 35 U.S.C. 154(b) by 357 days.

(21) Appl. No.: 11/996,310

(22) PCT Filed: Jul. 20, 2006

(86) PCT No.: PCT/EP2006/064461
§ 371 (c)(1),
(2), (4) Date: Jan. 21, 2008

(87) PCT Pub. No.: WO2007/010023
PCT Pub. Date: Jan. 25, 2007

(65) Prior Publication Data
US 2008/0226700 A1  Sep. 18, 2008

(30) Foreign Application Priority Data

Jul. 21, 2005  (IT) .............................. MI2005A1396

(51) Int. Cl.
*A61K 36/00* (2006.01)
*A61K 47/00* (2006.01)
*A61K 9/00* (2006.01)
*A61K 9/70* (2006.01)

(52) U.S. Cl. ......... 424/725; 424/449; 424/400; 424/439
(58) Field of Classification Search .................. None
See application file for complete search history.

(56) References Cited

U.S. PATENT DOCUMENTS

| 3,395,063 | A | * | 7/1968 | Ralha .............................. 156/295 |
| 4,288,433 | A | | 9/1981 | Koulbanis et al. |
| 6,891,063 | B1 | * | 5/2005 | Mora et al. ..................... 562/498 |
| 2001/0016213 | A1 | | 8/2001 | Singh-Verma |
| 2004/0121027 | A1 | | 6/2004 | Pushpangadan et al. |
| 2004/0122105 | A1 | | 6/2004 | Bettle et al. |
| 2008/0248074 | A1 | * | 10/2008 | Scott .............................. 424/402 |

FOREIGN PATENT DOCUMENTS

| DE | 20320103 | | 7/2004 |
| FR | 1966-37281 F | * | 7/1967 |
| WO | WO-03047609 | | 6/2003 |

OTHER PUBLICATIONS

Michael Derrida (What is Nettle (Urtica dioica, Urticae herba, Urticae radix)?, date Nov. 11, 2003, www.ccba.bc.ca/discuss1/disc1/000011la.htm).*

* cited by examiner

*Primary Examiner* — Christopher R Tate
*Assistant Examiner* — Randall Winston
(74) *Attorney, Agent, or Firm* — Gifford, Krass, Sprinkle, Anderson & Citkowski, P.C.

(57) ABSTRACT

The present invention relates to a medicated gauze containing as active ingredient, aliantoin, a *Centella asiatica* extract and, optionally, an *Urtica dioica* extract.

12 Claims, No Drawings

MEDICATED GAUZE

FIELD OF THE INVENTION

The present invention relates to a medicated gauze for tissue repair of cutaneous lesions.

STATE OF THE ART

The process of tissue repair of a cutaneous lesion, independently from the underlying cause, occurs by a sequence of events that is always identical and very complex, involving a high number of cells and chemical mediators.

This process is spontaneously activated following a cutaneous lesion.

Under certain conditions, however, the process of tissue repair is delayed, due to a persistent harmful stimulus and/or alterations of the biochemical and cellular balance, possibly leading to chronic cutaneous lesions.

For instance, these lesions are represented by ischemic, diabetic, venous ulcers and by decubitus lesions that do not reepithelize.

The treatment of chronic cutaneous lesions involves a triple therapeutic approach: general therapy, etiological therapy and local therapy. As far as local therapy is concerned, modern technology has set up a series of new concept medications, defined as "advanced", which unlike traditional medications, keep the wound in a moist microenvironment.

Among the latter type of medications, medicated gauzes turned out to be especially effective, and particularly the Fitostimoline Gauze® containing a Triticum vulgare extract as active principle.

Centella asiatica is a plant of Indian origin that is used, mostly as total triterpenic fraction, in many medicinal products for treatment of idiopathic or secondary chronic venous insufficiency and of varices complications, in delayed cicatrization and alterations of cutaneous trophism. The components of the total triterpenic fraction, which apparently accounts for the active fraction of Centella, are asiaticoside (40%), asiatic acid (30%) and madecassic acid (30%).

For instance, preparations for topical use, present on the market as powder or ointment, contain the total triterpenic fraction of Centella asiatica in an amount of 2 gm or 1 gm, respectively.

SUMMARY OF THE INVENTION

The present inventors have now found that when a Centella asiatica extract, containing not less than 4% of total triterpenic fraction, is used in association with allantoin, a synergistic effect is observed on the cicatrizant activity of both these active principles.

In fact, as illustrated in the following examples, gauzes impregnated with allantoin-containing ointment and with very low doses of Centella asiatica extract, that are much lower compared to those used in the above said medicinal products, show an efficacy in the treatment of cutaneous lesions that is tendentially superior to that of Fitostimoline Gauzes®.

Therefore, the present invention relates to an ointment suitable for preparation of a medicated gauze comprising as active principles allantoin, a Centella asiatica extract and, optionally, an Urtica dioica extract in association with dermatologically compatible excipients, and relates also to a gauze, preferably made of hydrophilic cotton, impregnated with the above said ointment.

Moreover, the present invention relates to the use of a mixture comprising allantoin, a Centella asiatica extract and, optionally, an Urtica dioica extract for preparation of a medicament, in the form of ointment or medicated gauze, for topical treatment of all dermal tissue alterations involving reactivation of epithelial neoformation processes.

DETAILED DESCRIPTION OF THE INVENTION

A first object of the present invention is an ointment suitable for preparation of a medicated gauze comprising as active principles allantoin and an extract obtained from Centella asiatica leaves, containing not less than 4% of total triterpenic fraction, estimated as asiaticoside, in association with dermatologically compatible excipients.

A preferred embodiment of the present invention involves, as additional active principle of the above said ointment, an extract from Urtica dioica containing at least 0.3% and preferably 0.4% of total sterols, estimated as β-sitosterol.

The above said extracts are preferably dry extracts.

When the above said ointment does not contain Urtica dioica, preferably it contains, by weight, from 0.15% to 0.6% of dry extract from Centella asiatica and from 0.4% to 1.6% of allantoin.

Alternately, in presence of a dry extract from Urtica dioica, the above said ointment contains, by weight, from 0.05% to 0.2% of dry extract from Centella asiatica, from 0.01% to 0.03% of dry extract from Urtica dioica and from 0.4% to 1.6% of allantoin.

Preferably, the above said ointment is based on polyethylene glycols. In the ointment of the present invention, particularly preferred is the use of a mixture of polyethylene glycols having a molecular weight of 400, 1500 and 4000 Da.

Moreover, the ointment according to the present invention contains dermatologically compatible excipients, as for instance antioxidants, preservatives, emulsifiers and humidifiers.

A further object of the present invention is a medicated sterile gauze consisting of a gauze uniformly impregnated with the above said ointment.

Preferably, the gauze of the present invention is an hydrophilic cotton gauze. As an alternative to the gauze of the present invention, it is possible to use polyurethane supports with modulable porosity, made of polyvinyl alcohol or non-woven tissue.

The medicated gauze of the present invention is impregnated with an amount of the above said ointment ranging from 0.03 to 0.05 gm per $cm^2$ and preferably equal to 0.04 gm per $cm^2$.

The gauze according to present invention is stored in an hermetically sealed aluminium bag in order to maintain sterility.

As shown in the following experimental examples, the medicated gauze, according to present invention, is especially effective in inducing reepithelization of cutaneous lesions. In fact, the combination of allantoin and Centella asiatica extract produces a synergy suitable to support the reepithelization process, that is further stimulated if an Urtica dioica extract is also added.

Therefore, a further object of the present invention is the use of a mixture of allantoin, Centella asiatica extract and, optionally, Urtica dioica extract for the preparation of a medicament, preferably in the form of medicated gauze, for topical treatment of cutaneous lesions, particularly chronic cutaneous lesions.

According to a particularly preferred embodiment, the medicated gauze of the present invention is especially effective on ulcero-dystrophic alterations (varicose ulcers, decubitus sores, torpid sores, fistula tracts, rhagades etc.); burns; lesions resulting from delayed post-operative cicatrization and abrasions.

Preferably, treatment of the above said lesions with the medicated gauze of the present invention requires at least one or two daily applications on the lesion.

The present invention will be now better illustrated by the following examples.

Example 1

A medicated gauze was prepared by soaking a hydrophilic cotton gauze in 0.04gm/cm² ointment having the following percent composition

|  | Percentage by weight |
| --- | --- |
| D.E. *Centella Asiatica* | 0.30% |
| Allantoin powder | 0.8% |
| PEG 400 | 35% |
| PEG 1500 | 16% |
| PEG 4000 | 16% |
| Sorbitol | 7.25% |
| Water | 14.9% |
| Menthol | 0.02% |
| Glycerol | 4.5% |
| Vaseline | 2.2% |
| Cetylic Alcohol | 0.75% |
| Stearylic Alcohol | 0.75% |
| O.e cinnamon | 0.01% |
| Phenoxyethanol | 1% |
| Tocopherol Acetate | 0.5% |

Example 2

A medicated gauze was prepared by soaking a hydrophilic cotton gauze in 0.04gm/cm² ointment having the following percent composition

|  | Percentage by weight |
| --- | --- |
| D.E. *Centella Asiatica* | 0.10% |
| D.E. *Urtica Dioica* | 0.01% |
| Allantoin powder | 0.80% |
| PEG 400 | 35% |
| PEG 1500 | 16% |
| PEG 4000 | 16% |
| Sorbitol | 7.26% |
| Water | 14.9% |
| Menthol | 0.02% |
| Glycerol | 4.5% |
| Vaseline | 2.2% |
| Cetylic Alcohol | 0.75% |
| Stearylic Alcohol | 0.75% |
| O.e cinnamon | 0.005% |
| Phenoxyethanol | 1% |
| Tocopherol Acetate | 0.50% |

Example 3

Clinical Investigation

Evaluation of the efficacy of the products illustrated in examples 1 and 2 was done on chronic cutaneous lesions. In the following, we will refer for simplicity to the product in example 1. However, identical tests with identical results have been made also on the product in example 2.

The investigation was made on 40 patients (32 women with a mean age of 77 years and 8 men with a mean age of 76 years) with cutaneous lesions of size smaller than 20 cm², not infected and characterized by stage I or II depth.

The depth of cutaneous lesions has been classified as follows:

Stage I: superficial lesion, which does not cross the dermal layer of skin;

Stage II: medium lesion, affecting only the subcutaneous layer.

Patients have been divided into two homogeneous groups of 20 patients each, based on age, type, stage and surface of the lesion, as well as perilesional edge. The first group of patients has been treated with the impregnated gauze of example 1, while the second group has been treated with Fitostimoline Gauzes© (gauzes saturated with 4 gm of cream containing in 100 gm: 15 gm aqueous extract from *Triticum vulgare*, with 200 mg/100 ml dry residue, and 1 gm 2-phenoxyethanol).

Table I shows the type of lesions in patients belonging to the two groups:

| Type of lesion | Gauze example 1 group Number of patients | Fitostimoline gauze group Number of patients |
| --- | --- | --- |
| Venous ulcer | 6 | 7 |
| Vasculitic ulcer | 4 | 2 |
| Mixed ulcer | 4 | 4 |
| Post-traumatic ulcer | 4 | 3 |
| Post-surgical ulcer | 1 | 0 |
| Pressure ulcer | 1 | 4 |

Before starting the treatment, all ulcers were subjected to normal cleansing; moreover, all patients started a specific medical therapy for the concomitant pathology.

All patients underwent two daily medications with the gauze of example 1 or with the Fitostimoline gauze for four weeks. Evaluation of the state of cutaneous lesion has been made at baseline, before treatment and in subsequent weekly controls, throughout the observation period, taking in consideration the following parameters during the control visits: area and diameters of the lesion in centimetres, aspect of background, margins and depth of the lesion.

For each lesion, the daily reepithelization index was calculated (IGR), expressing the daily percent reepithelization as cm² of the lesion.

This index is calculated according to the following formula:

$$IGR = \frac{Ext\ T_o - Ext\ T_x}{Ext\ T_o} \bigg/ X$$

where

Ext $T_o$: extent of the lesion at the beginning of the treatment

Ext $T_x$: extent of the lesion after x days of treatment

X: days of treatment

A clinical judgement on the progress of the cicatrization process has been then assigned, based on the criteria summarized in table II:

| Clinical judgement | IGR | % reepithelization at the end of treatment |
|---|---|---|
| Excellent | IGR ≧ 0.032 | ≧90% 90% of the lesion area |
| Good | 0.018 ≦ IGR < 0.032 | ≧50% of the lesion area |
| Mediocre | 0.004 ≦ IGR < 0.018 | ≧10% of the lesion area |
| Unchanged | 0.000 ≦ IGR < 0.004 | <10% of the lesion area |
| Worsened | IGR < 0 | Increase of the lesion area compared to baseline |
| Not assessable | IGR not determined | Drop out |

For a better evaluation of the results, the two study groups have been each divided into four subgroups, based on the extent of the lesion at the beginning of the treatment (Ext $T_0$ in cm$^2$), as shown in the table III:

| Gauze example 1 Group | | | Fitostimoline Group | |
|---|---|---|---|---|
| Subgroup | Patients No. | Range for Ext $T_0$ | Patients No. | Subgroup |
| A1 | 9 | 1,00 ≦ Est $T_0$ < 5,000 | 10 | F1 |
| A2 | 5 | 5,00 ≦ Est $T_0$ < 10,00 | 5 | F2 |
| A3 | 4 | 10,00 ≦ Est $T_0$ < 15,00 | 3 | F3 |
| A4 | 2 | 15,00 ≦ Est $T_0$ < 20,00 | 2 | F4 |

Comparison Between the Results Obtained from the Two Study Groups:

Table IV shows a comparison between clinical judgements obtained from the two study groups, for each subgroup:

| Subgroup | Clinical judgement | Gauze Ex. 1 Group | Fitostimoline gauze Group |
|---|---|---|---|
| A1-F1 | Excellent | 5 | 4 |
| | Good | 1 | 3 |
| | Mediocre | 2 | 2 |
| | Unchanged | 1 | 1 |
| | Worsened | 0 | 0 |
| | Not assessable | 0 | 0 |
| A2-F2 | Excellent | 0 | 0 |
| | Good | 4 | 3 |
| | Mediocre | 1 | 2 |
| | Unchanged | 0 | 0 |
| | Worsened | 0 | 0 |
| | Not assessable | 0 | 0 |
| A3-F3 | Excellent | 1 | 0 |
| | Good | 2 | 1 |
| | Mediocre | 1 | 2 |
| | Unchanged | 0 | 0 |
| | Worsened | 0 | 0 |
| | Not assessable | 0 | 0 |
| A4-F4 | Excellent | 0 | 0 |
| | Good | 1 | 1 |
| | Mediocre | 1 | 1 |
| | Unchanged | 0 | 0 |
| | Worsened | 0 | 0 |
| | Not assessable | 0 | 0 |

Table V shows a comparison between the global clinical judgement obtained from the two study groups:

| Clinical judgement | Gauze example 1 Group | Fitostimoline Group |
|---|---|---|
| Excellent | 6 | 4 |
| Good | 8 | 8 |
| Mediocre | 4 | 5 |
| Unchanged | 2 | 3 |
| Worsened | 0 | 0 |
| Not assessable | 0 | 0 |

Satisfactory results have been obtained in both study groups.

However, better results have been obtained with the gauze according to the present invention.

In particular, daily reepithelization index values were on average higher than those obtained with Fitostimoline gauzes, regardless of the extent and typology of the lesion.

The invention claimed is:

1. A composition in the form of an ointment for treating cutaneous lesions comprising a mixture of principles in combination with dermatologically compatible excipients, wherein said active principles consist essentially of a *Centella asiatica* extract containing at least 4% by weight of total triterpenic fraction, an *Urtica dioica* extract containing at least 0.3% by weight of total sterols and allantoin, and wherein said extracts are dry extracts and wherein the dry extract of *Centella asiatica* is from 0.05% to 0.2% by weight, the dry extract of *Urtica dioica* is from 0.01% to 0.03% by weight and allantoin is from 0.4% to 1.6% by weight.

2. The composition according to claim 1, wherein said *Centella asiatica* extract contains 4% by weight of total triterpenic fraction.

3. The composition according to claim 1, wherein said *Urtica dioica* extract contains 0.4% by weight of total sterols.

4. The composition according to claim 1 further comprising polyethylene glycols.

5. The composition according to claim 4, wherein said polyethylene glycols are a mixture of polyethylene glycols having molecular weights of 400, 1500 and 4000 Da.

6. A sterile medicated gauze uniformly impregnated with the composition according to claim 1.

7. The sterile medicated gauze according to claim 6, made of hydrophilic cotton.

8. The sterile medicated gauze according to claim 6, impregnated with an amount of said ointment comprised between 0.03 and 0.05 g per cm$^2$.

9. The sterile medicated gauze according to claim 8 wherein said amount of ointment is 0.04 g per cm$^2$.

10. A method for topical treatment of cutaneous lesions comprising administering to a patient in need thereof an effective amount of the composition according to claim 1.

11. The method according to claim 10, wherein said cutaneous lesions are chronic cutaneous lesions.

12. The method according to claim 10, wherein said cutaneous lesions are ulcero-dystrophic alterations (varicose ulcers, decubitus sores, torpid sores, fistula tracts, rhagades etc.) burns, lesiions resulting from delayed post-operative cicatrization and abrasions.

* * * * *

UNITED STATES PATENT AND TRADEMARK OFFICE
CERTIFICATE OF CORRECTION

| | | |
|---|---|---|
| PATENT NO. | : 7,923,042 B2 | Page 1 of 1 |
| APPLICATION NO. | : 11/996310 | |
| DATED | : April 12, 2011 | |
| INVENTOR(S) | : Guglielmo Cozzolino | |

It is certified that error appears in the above-identified patent and that said Letters Patent is hereby corrected as shown below:

At column 1, line number 26, "therapy.As" should read --therapy. As--.
At column 1, line number 32, "Gauze®" should read --gauze®--.
At column 1, line number 34, "asiatica" should read --Asiatica--.
At column 1, line number 44, "asiatica" should read --Asiatica--.
At column 1, line number 50, "asiatica" should read --Asiatica--.
At column 1, line number 56, "asiatica" should read --Asiatica--.
At column 1, line number 60, "Gauzes®" should read --gauzes®--.
At column 1, line number 63, "asiatica" should read --Asiatica--.
At column 2, line number 2, "asiatica" should read --Asiatica--.
At column 2, line number 13, "asiatica" should read --Asiatica--.
At column 2, line number 23, "asiatica" should read --Asiatica--.
At column 2, line number 27, "asiatica" should read --Asiatica--.
At column 2, line number 56, "asiatica" should read --Asiatica--.
At column 2, line number 61, "asiatica" should read --Asiatica--.
At column 4, line number 18, "Gauzes©" should read --gauzes©--.
At column 6, line number 24, "asiatica" should read --Asiatica--.
At column 6, line number 28, "asiatica" should read --Asiatica--.
At column 6, line number 32, "asiatica" should read --Asiatica--.
At column 6, line number 58, "lessions" should read --lesions--.

Signed and Sealed this
Eleventh Day of December, 2012

David J. Kappos
*Director of the United States Patent and Trademark Office*